(12) United States Patent
Whitehurst

(10) Patent No.: US 6,645,230 B2
(45) Date of Patent: Nov. 11, 2003

(54) THERAPEUTIC LIGHT SOURCE AND METHOD

(75) Inventor: Colin Whitehurst, Altrincham (GB)

(73) Assignee: Photo Therapeutics Ltd., Alfrincham (GB)

( * ) Notice: Subject to any disclaimer, the term of this patent is extended or adjusted under 35 U.S.C. 154(b) by 69 days.

(21) Appl. No.: 09/815,348

(22) Filed: Mar. 23, 2001

(65) Prior Publication Data

US 2002/0029071 A1 Mar. 7, 2002

(30) Foreign Application Priority Data

Mar. 23, 2000 (GB) .............................................. 0007085
Apr. 17, 2000 (GB) .............................................. 0009491
Dec. 19, 2000 (GB) .............................................. 0030974

(51) Int. Cl.$^7$ .............................................. A61N 31/30
(52) U.S. Cl. ...................................................... 607/88
(58) Field of Search .............................. 607/80, 88, 90, 607/92, 93

(56) References Cited

U.S. PATENT DOCUMENTS

| | | | | |
|---|---|---|---|---|
| 4,335,724 A | * | 6/1982 | Frei et al. ................. | 250/494.1 |
| 4,660,561 A | * | 4/1987 | Nielsen ...................... | 607/91 |
| 4,740,707 A | * | 4/1988 | Thaw ......................... | 250/494.1 |
| 4,761,047 A | * | 8/1988 | Mori .......................... | 36/137 |
| 4,822,335 A | | 4/1989 | Kawai et al. | |
| 4,907,132 A | * | 3/1990 | Parker ........................ | 362/31 |
| 4,930,504 A | | 6/1990 | Diamantopoulos et al. | |
| 4,953,549 A | * | 9/1990 | Mori ....................... | 250/227.11 |

(List continued on next page.)

FOREIGN PATENT DOCUMENTS

| | | | | |
|---|---|---|---|---|
| EP | 0 158 025 A1 | 10/1985 | ............ | A61N/5/06 |
| EP | 0 266 038 A2 A3 | 5/1988 | ............ | A61N/5/06 |
| EP | 0 320 080 A1 | 6/1989 | ............ | A61N/5/06 |
| EP | 0 860 179 A2 A3 | 8/1998 | ............ | A61N/5/06 |
| EP | 1 024 327 A1 | 8/2000 | ............ | F21V/33/00 |
| GB | 2 287 652 A | 9/1995 | ............ | A61N/5/06 |
| GB | 2 331 399 A | 5/1999 | ............ | A61N/5/06 |
| GB | 2 356 570 A | 5/2001 | ............ | A61N/5/06 |
| GB | 2 368 020 A | 4/2002 | ............ | A61N/5/06 |
| GB | 2 370 229 A | 6/2002 | ............ | A61N/5/06 |
| WO | WO 93/09847 A1 | 5/1993 | ............ | A61N/5/06 |
| WO | WO 93/21842 A1 | 11/1993 | ............ | A61B/17/36 |
| WO | WO 95/19808 A1 | 7/1995 | ............ | A61N/5/06 |
| WO | WO 95/26217 A1 | 10/1995 | ............ | A61N/5/06 |
| WO | WO 98/07379 A1 | 2/1998 | ............ | A61B/17/41 |
| WO | WO 98/43703 A1 | 10/1998 | ............ | A61N/5/06 |
| WO | WO 99/10046 A1 | 3/1999 | ............ | A61N/5/00 |
| WO | WO 99/19024 A1 | 4/1999 | ............ | A61N/5/06 |
| WO | WO 00/15296 A1 | 3/2000 | ............ | A61N/5/00 |
| WO | WO 01/14012 A1 | 3/2001 | ............ | A61N/5/06 |
| WO | WO 01/45795 A1 | 6/2001 | ............ | A61N/5/06 |

OTHER PUBLICATIONS

English–language Abstract for EP 0 860 179 A2&A3, printed from DIALOG File 348: European Patents, 2 pages.

*Primary Examiner*—Derek Boles
(74) *Attorney, Agent, or Firm*—Sterne, Kessler, Goldstein & Fox P.L.L.C.

(57) ABSTRACT

A therapeutic light source, for example for photodynamic therapy (PDT), comprises an air-cooled array of LED's ($L_{x,y}$), the air being vented in the vicinity of the array. The array may be mounted at the distal end of a hand piece suitable for invasive therapy. The LED's may be coupled to a light guide (W, L). The emission spectra of the LED's may be substantially limited to the range 550 to 660 nm, and preferably to one of the ranges 590 to 640 nm, 560 to 644 nm, 650 to 660 nm, and 550 to 570 nm. The therapeutic light source may comprise a non-planar array of light-emitting diodes L conforming with the shape of an external area to be treated or diagnosed. The therapeutic light source may comprise a non-planar array of independently switchable red and blue light-emitting diodes $L_R$, $L_B$, mounted on a flexible backing.

15 Claims, 12 Drawing Sheets

U.S. PATENT DOCUMENTS

| | | | |
|---|---|---|---|
| 4,974,922 A | * 12/1990 | Mori | 385/147 |
| 5,278,432 A | 1/1994 | Ignatius et al. | |
| 5,304,207 A | 4/1994 | Stromer | |
| 5,354,322 A | * 10/1994 | Miyano | 600/182 |
| 5,358,503 A | 10/1994 | Bertwell et al. | |
| 5,409,482 A | * 4/1995 | Diamantopoulos | 606/10 |
| 5,500,009 A | 3/1996 | Mendes et al. | |
| 5,511,563 A | * 4/1996 | Diamond | 128/898 |
| 5,549,660 A | 8/1996 | Mendes et al. | |
| 5,601,619 A | * 2/1997 | Drechsler | 607/88 |
| 5,616,140 A | * 4/1997 | Prescott | 606/10 |
| 5,634,711 A | 6/1997 | Kennedy et al. | |
| 5,660,461 A | 8/1997 | Ignatius et al. | |
| 5,702,432 A | 12/1997 | Chen et al. | |
| 5,709,645 A | 1/1998 | Siever | |
| 5,728,090 A | 3/1998 | Martin et al. | |
| 5,766,233 A | 6/1998 | Thiberg | |
| 5,775,339 A | 7/1998 | Woodburn et al. | |
| 5,800,478 A | * 9/1998 | Chen et al. | 606/14 |
| 5,814,008 A | * 9/1998 | Chen et al. | 604/113 |
| 5,820,625 A | * 10/1998 | Izawa et al. | 606/13 |
| 5,876,427 A | 3/1999 | Chen et al. | |
| 5,913,883 A | * 6/1999 | Alexander et al. | 606/10 |
| 5,944,748 A | * 8/1999 | Mager et al. | 607/88 |
| 5,957,959 A | * 9/1999 | Rissmaney et al. | 250/494.1 |
| 5,957,960 A | 9/1999 | Chen et al. | |
| 5,968,033 A | 10/1999 | Fuller et al. | |
| 5,989,283 A | 11/1999 | Wilkens | |
| 5,997,569 A | * 12/1999 | Chen et al. | 607/115 |
| 6,024,760 A | 2/2000 | Marchesi | |
| 6,063,108 A | 5/2000 | Salansky et al. | |
| 6,074,382 A | 6/2000 | Asah et al. | |
| 6,094,595 A | 7/2000 | Takahashi | |
| 6,096,066 A | * 8/2000 | Chen et al. | 607/88 |
| 6,107,466 A | 8/2000 | Hasan et al. | |
| 6,110,195 A | * 8/2000 | Xie et al. | 606/10 |
| 6,143,287 A | 11/2000 | Ben-Hur et al. | |
| 6,171,331 B1 | 1/2001 | Bagraev et al. | |
| 6,183,500 B1 | * 2/2001 | Kohler | 607/88 |
| 6,187,029 B1 | 2/2001 | Shapiro et al. | |
| 6,190,376 B1 | 2/2001 | Asah et al. | |
| 6,221,095 B1 | 4/2001 | Van Zuylen et al. | |
| 6,235,046 B1 | 5/2001 | Gerdt | |
| 6,238,424 B1 | 5/2001 | Thiberg | |
| 6,238,425 B1 | 5/2001 | Thiberg | |
| 6,238,426 B1 | 5/2001 | Chen | |
| 6,249,698 B1 | 6/2001 | Parris | |
| 6,269,818 B1 | * 8/2001 | Lui et al. | 128/898 |
| 6,290,713 B1 | 9/2001 | Russell | |
| 6,306,160 B1 | 10/2001 | Nidetzky | |
| 6,383,177 B1 | 5/2002 | Balle-Petersen et al. | |
| 6,402,774 B1 | * 6/2002 | Caldironi | 128/898 |

* cited by examiner

THERAPEUTIC LIGHT SOURCE AND METHOD

The present invention relates to a non-coherent light source for use in therapy such as photodynamic therapy (PDT), particularly using light emitting diodes (LED's).

Photodynamic therapy involves the administration of a photosensitising drug to an affected area, and its subsequent irradiation with light—see for example 'The Physics of Photodynamic Therapy' by B C Wilson and M S Patterson, Physics in Medicine & Biology 31 (1986) April No. 4, London GB.

The document GB 2,212,010 discloses a therapeutic light source which uses an array of discrete LED's as an alternative to lasers or laser diodes. The output of the LED's is focussed so as to provide the necessary intensity.

The document WO 94/15666 discloses a therapeutic light source specifically for PDT, with an integrated array of LED's mounted on the distal end of a hand piece. The LED's are overdriven to give the necessary intensity, and cooled by the flow of water around a closed loop passing along the hand piece. The document U.S. Pat. No. 5,728,090 discloses a somewhat similar device with various different types of head containing integrated LED matrices. These devices require complicated liquid cooling circuits which would add to the cost of the device and add to the bulk of the hand piece, which is disadvantageous for invasive use.

The document U.S. Pat. No. 5,728,090 mentions that the wavelength of the LED's is between 300 nm and 1300 nm and is selected based upon the particular photosensitive dye used during PDT. However, the wavelengths of LED's capable of providing the necessary intensity for PDT cannot freely be chosen within that range.

According to one aspect of the present invention, there is provided a light source for therapy and/or diagnosis, comprising a non-planar array of light-emitting diodes conforming with the shape of an external area to be treated or diagnosed.

According to another aspect of the present invention, there is provided a light source for therapy and/or diagnosis, comprising a first array of light-emitting diodes and a second array of light emitting diodes movably connected thereto.

According to another aspect of the present invention, there is provided a light source for therapy and/or diagnosis, comprising an array of light-emitting diodes mounted on the curved inner surface of a housing arranged to cover at least part of the length of a patient.

According to another aspect of the present invention, there is provided a light source for therapy or diagnosis of a patient, comprising an array of light-emitting diodes arranged within a housing, and an aperture allowing a part of the patient's body to be inserted into the housing, the array being arranged to direct light onto the part of the patient's body when inserted into the housing.

According to another aspect of the present invention, there is provided a light source for therapy or diagnosis of a patient, comprising an array of light-emitting diodes arranged within a sleeve so as to direct light onto part of an arm and/or hand of a patient when inserted into the sleeve.

According to another aspect of the present invention, there is provided a light source for therapy or diagnosis of a patient, comprising an intraluminal probe carrying on the surface thereof an array of discrete light-emitting diodes.

According to another aspect of the present invention, there is provided a therapeutic light source comprising an air-cooled array of LED's, the air being vented in the vicinity of the array. In one embodiment, the array is mounted at the distal end of a hand piece suitable for invasive therapy.

According to another aspect of the present invention, there is provided a therapeutic light source comprising an array of LED's coupled to a light guide for delivering the light to the area to be treated. Preferably, the LED's are directly coupled without intervening optical devices.

According to another aspect of the present invention, there is provided a therapeutic light source comprising an array of LED's with emission spectra substantially limited to the range 550 to 660 nm, and preferably to one of the ranges 590 to 640 nm, 560 to 644 nm, 650 to 660 nm, and 550 to 570 nm.

According to another aspect of the present invention, there is provided a therapeutic light source comprising an array of LED's with peak emission spectra of approximately 430 nm, 470 nm, 505 nm or 525 nm.

Specific embodiments of the present invention will now be described with reference to the accompanying drawings, in which.

Figure 22A:
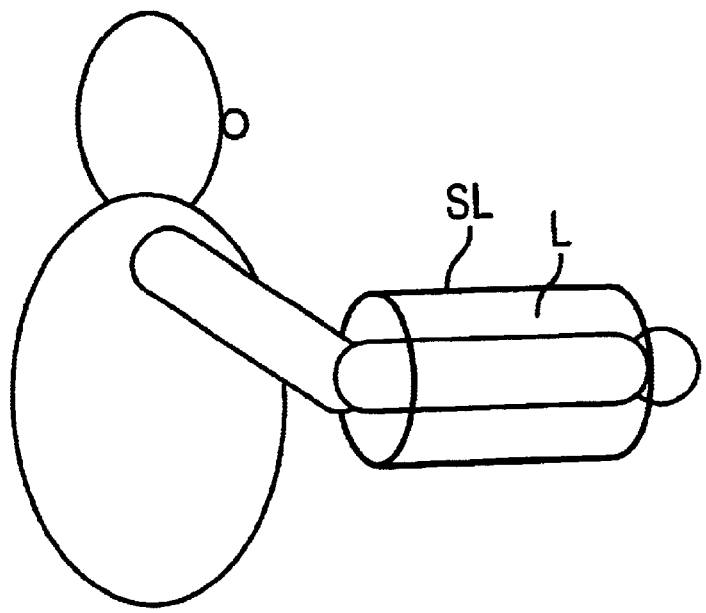
Figure 22B:
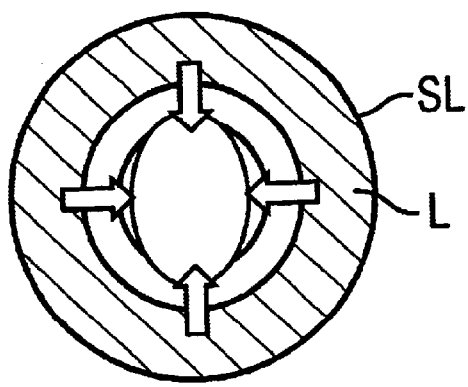
Figure 22C:
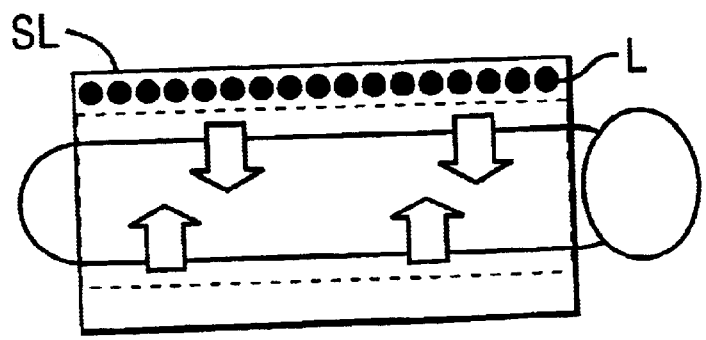
Figure 23A:
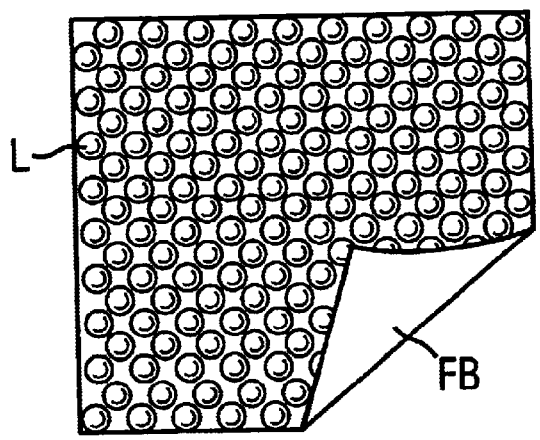
Figure 23B:
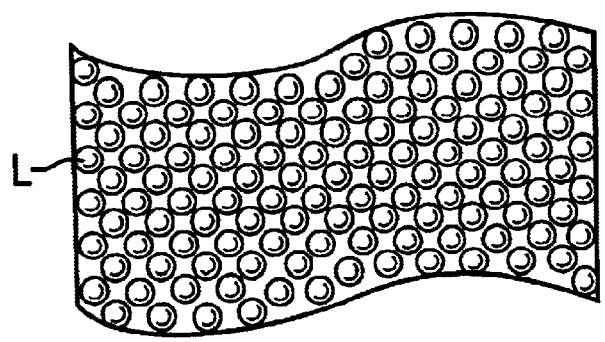
Figure 23C:
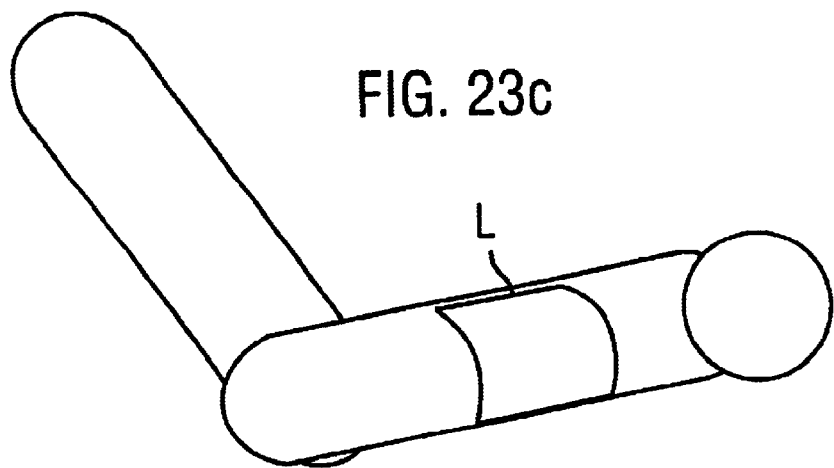
Figure 24:
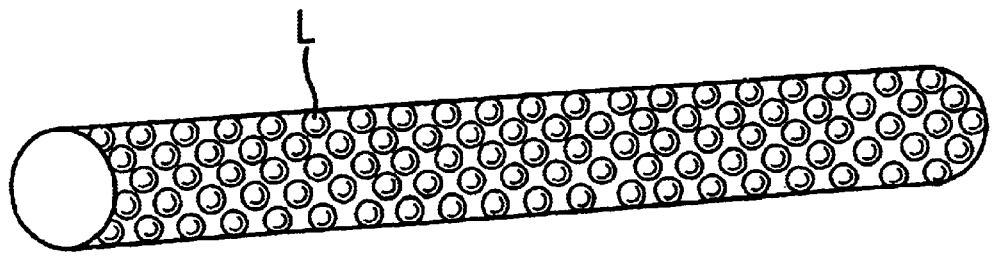
Figure 25:
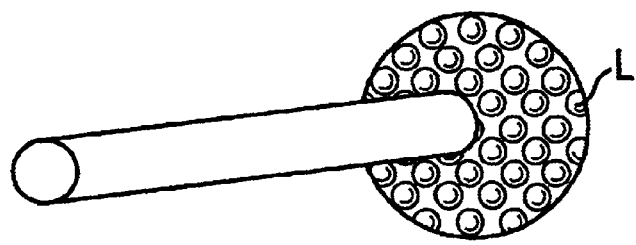
Figure 26:
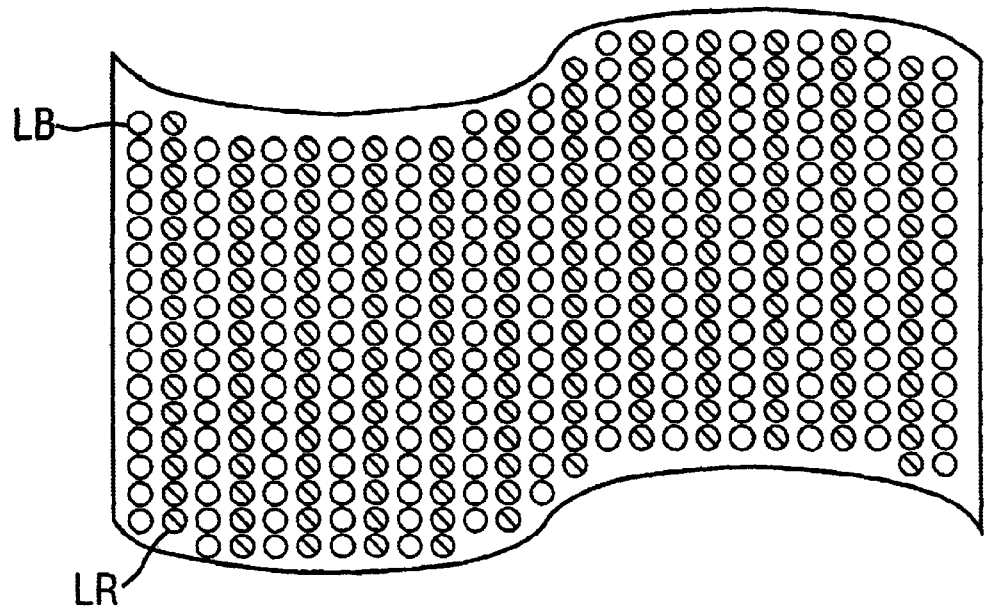

FIGS. 22*a*, 22*b* and 22*c* show respectively a side view, a transverse cross-section and a longitudinal cross-section of an LED array arranged within a sleeve in a eighteenth embodiment, for treatment of the hand, forearm and/or elbow;

FIGS. 23*a*, 23*b* and 23*c* show respectively two different shapes of flexible LED array, and a flexible array applied as a patch onto the skin of a patient, in an nineteenth embodiment;

FIG. 24 shows an LED array arranged on the side of a cylindrical intraluminal probe in a twentieth embodiment;

FIG. 25 shows an LED array arranged on the surface of a spherical intraluminal probe in a twenty-first embodiment; and FIG. 26 shows a more specific example of the flexible LED array in the nineteenth embodiment.

In a therapeutic light source in the first embodiment, as illustrated in FIGS. 1 to 5, light is emitted from a parallel-series matrix of LED's L connected through a current-limiting resistor R to a source of a voltage+V. The LED matrix is mounted on a heatsink array H parallel to and spaced apart from a fan array F by support rods R. Air is blown by the fan array F onto the back of the heatsink array H.

Figure 3:
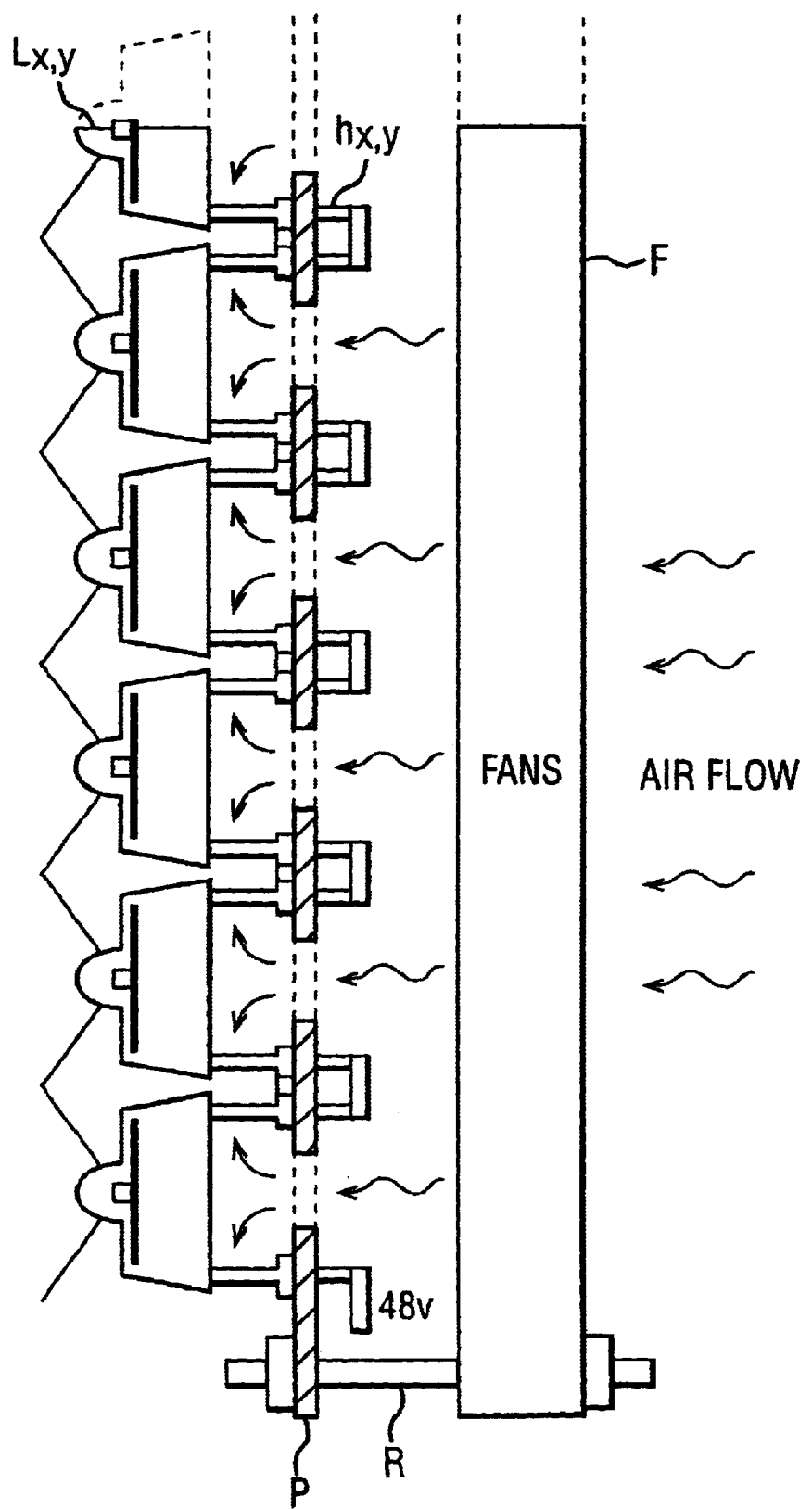
FIG. 3 is a cross section of part of the first embodiment.

As shown in more detail in FIG. 3, the heatsink array H comprises a plurality of individual heatsinks h mounted on the ends of the legs of the LED's, which pass through a support plate P. Each leg is soldered to an adjacent leg of another of the LED's in the same column. The support plate P is perforated to allow air to flow more freely around the heatsinks h and the LED's L.

The LED's L are arranged so as to produce a substantially uniform illumination of ±10% or less across a treatment field by selecting the beam divergence and spacing of the LED's L so that their individual beams overlap without causing substantial peaks or troughs in intensity. In the example shown in FIG. 4, uniformity of ±6% is achieved. In this embodiment, no optical system is needed between the LED's and the patient; instead, the light is emitted directly from the LED's onto the patient. As the light is not concentrated by any optical system, the LED's have individual power outputs of at least 5 mW and preferably at least 10 mW, to give the necessary fluence rates in the treatment field of at least 30 mW/cm$^2$ in the red region of the spectrum and at least 10 mW/cm$^2$ in the blue region.

In one specific example, a 15 cm diameter array of 288 'Super flux' LED's was used to produce a total light output of 8 W at 45 mW/cm$^2$ in the treatment field. The LED's were driven at a higher current load than their specification while being cooled by forced air convection from the fans F. In the specific example, the current was limited to 90 mA per column of diodes, but may be increased to 120 mA or more if increased light output is needed. The number of diodes in series, in each column, is selected so that the total forward operating voltage is as close as possible to, but less than, the power supply output voltage, in this case 48 V. This arrangement avoids wasteful in-circuit heating and maximizes the operating efficiency of the electrical system.

A method of treatment for oncological and non-oncological skin diseases such as cases of actinic/solar keratoses, Bowen's disease, superficial basal cell carcinoma, squamous cell carcinoma, intraepithelial carcinoma, mycosis fungoides, T-cell lymphoma, acne and seborrhoea, eczema, psoriasis, nevus sebaceous, gastrointestinal conditions (e.g. Barratt's oesophagus and colorectal carcinomas), gynaecological disorders (e.g. VIN, CIN and excessive uterine bleeding), oral cancers (e.g. pre-malignant or dyplastic lesions and squamous cell carcinomas), viral infections such as herpes simplex, molluscum contagiosum, and warts (recalcitrant, verruca vulgaris or verruca plantaris), alopecia areata, or hirsutism, using the first embodiment, will now be described. A cream or solution containing a photosensitising drug such as 5-ALA is applied topically under medical supervision to the affected area of the skin of the patient, or administered intravenously or orally. In another method of application for large areas, the patient may be immersed in a bath of solution. The affected area may then be covered for a period of 3 to 6 hours, or up to 24 hours if the treatment is to be continued the next day, to prevent removal of the drug and carrier, or activation by sunlight. The area is then uncovered and exposed to light from the lamp according to the first embodiment for a period of 15 to 30 minutes. The treatment may then be repeated as necessary, for a total of 1 to 3 treatments. This method is particularly suitable for the treatment of patients with very large lesions or multiple lesions extending over a large area.

Figure 4:
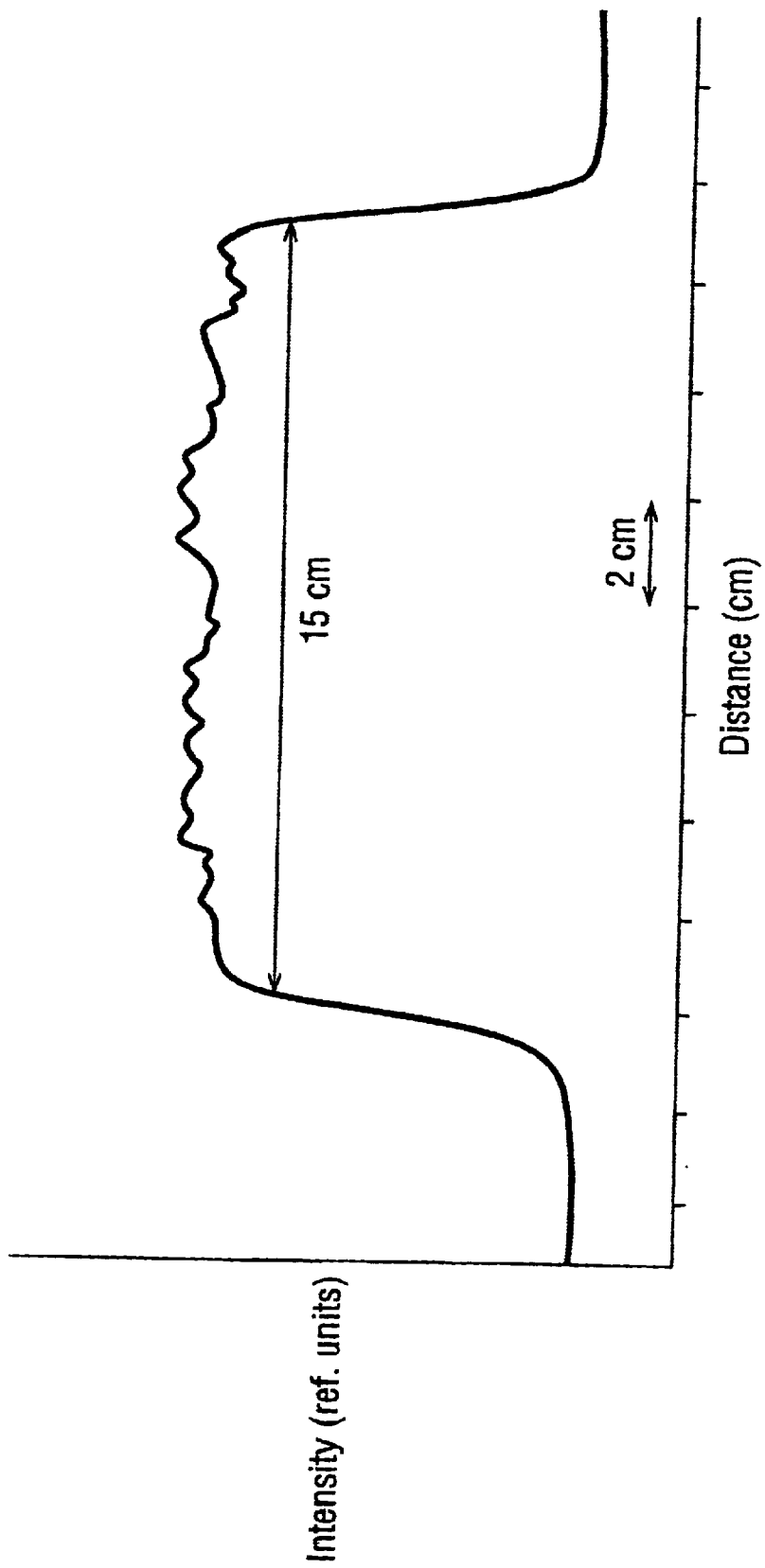
FIG. 4 is a graph showing the variation of intensity in a cross-section of the output of the first embodiment.

In a method of treatment using the device of the first embodiment, the LED array is positioned approximately parallel to an external affected area of a patient to be treated, with a separation sufficient to achieve the uniform illumination as shown in FIG. 4, for example 2 to 5 cm. The device may also be used for cosmetic or partially cosmetic treatment with a photosensitizing drug for portwine stain removal and hair restoration/removal, and without a photosensitizing drug for skin rejuvenation, wrinkle removal or biostimulation (including wound healing).

The lamp may also be used for fluorescence detection (photodiagnosis).

Figure 1:
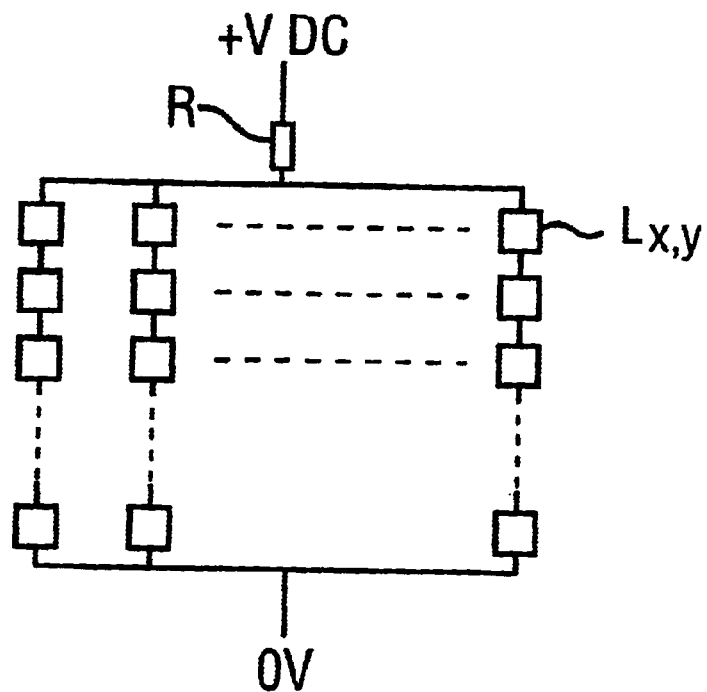
FIG. 1 is a diagram of a parallel-series matrix of discrete LED's used in first and second embodiments of the present invention.
Figure 5:
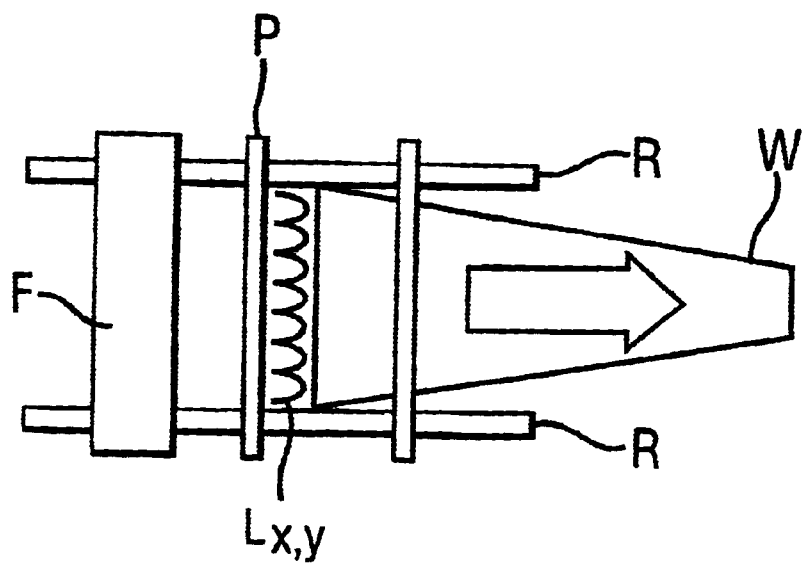
FIG. 5 is a cross-sectional diagram of a second embodiment.
Figure 2:
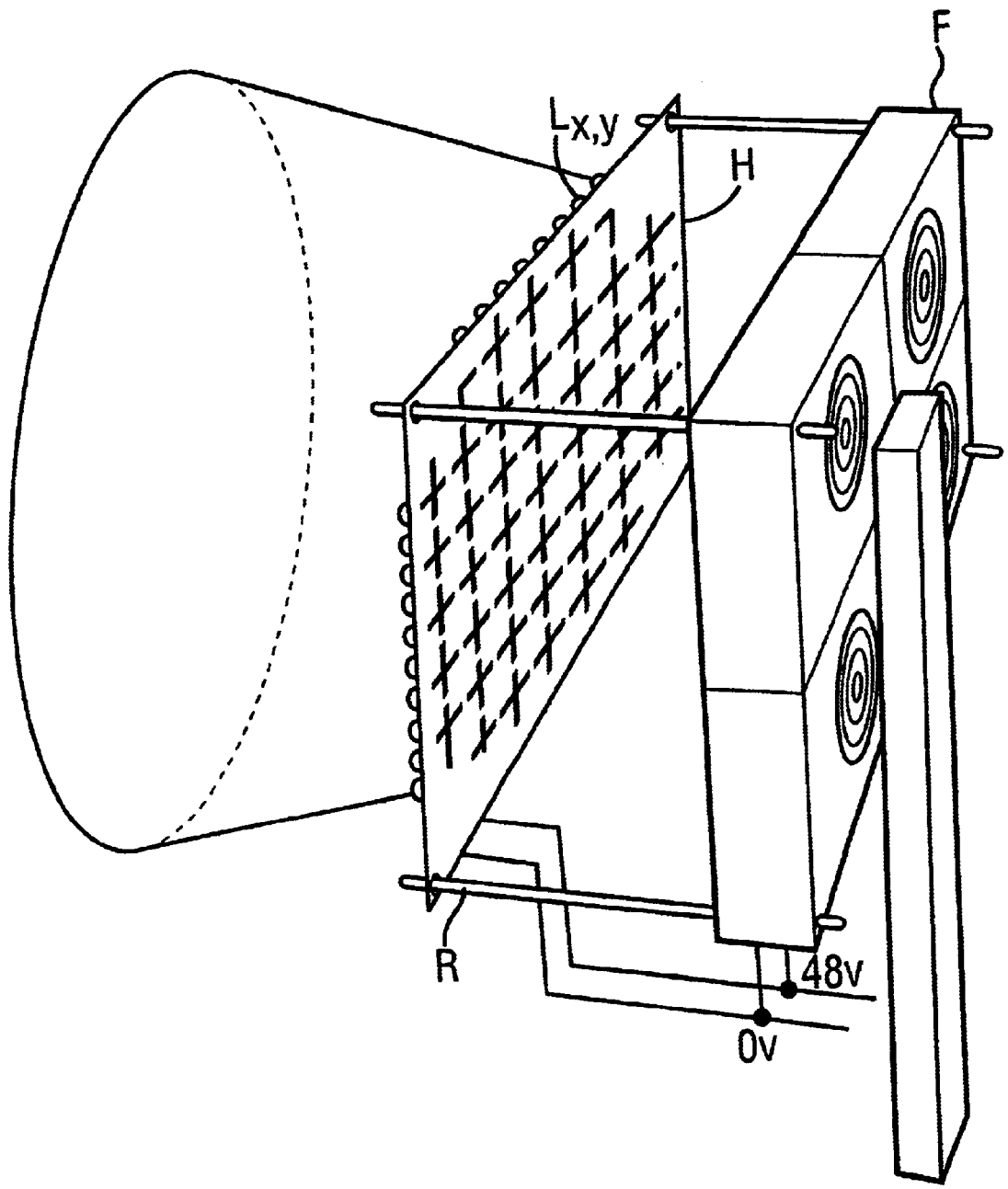
FIG. 2 is perspective diagram of the first embodiment.

The first embodiment may be modified in a second embodiment, as shown in FIG. 5, by the addition of a frusto-conical waveguide W, for example of acrylic (e.g. Perspex™) or glass, supported by the support rods R, which are extended in this embodiment. The waveguide W is arranged to concentrate light emitted by the LED's onto a smaller area with higher intensity. This arrangement is suitable for treating smaller external surfaces.

Figure 6:
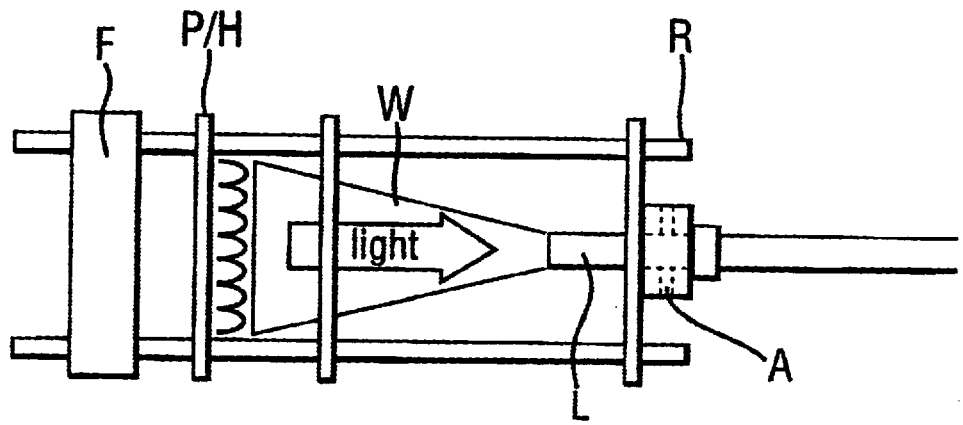
FIG. 6 is a cross-sectional diagram of a third embodiment.

The second embodiment may be modified in a third embodiment, as shown in FIG. 6, to deliver the light from the waveguide W into a lightguide L for internal treatment. The lightguide L, such as an optical fibre or fibre bundle, or liquid light guide, is held in a lightguide receptacle or adapter A, that is compatible for example with Olympus, Storz, ACMI or Wolf light cable fittings, in abutment or immediately adjacent relation with the narrow end of the waveguide W. The lightguide L may be of 3, 5 or 8 mm diameter. The support rods R align the optical axes of the waveguide W and lightguide L, so that the light emitted by the waveguide W is launched into the lightguide L. In the third embodiment, the light is concentrated by the waveguide and emitted over a small area at the distal end of the lightguide L which may be inserted into body cavities for oral, gynaecological, gastrointestinal or intraluminal treatment.

Figure 7:
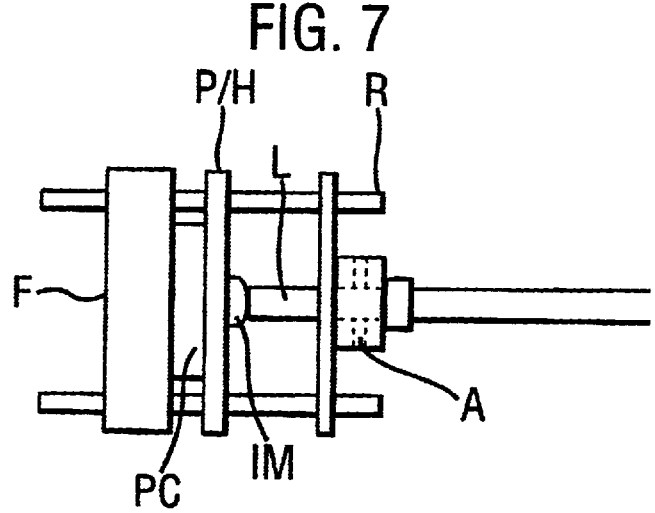
FIG. 7 is a cross-sectional diagram of a fourth embodiment.

The third embodiment may be modified in a fourth embodiment, as shown in FIG. 7, in which the discrete LED array is replaced by an integrated multi-die LED matrix IM (for example part no. OD 6380, OD 6624 or OD 6680 available from AMS Optotech, Bristol, UK) mounted on the support plate/heatsink P, H. A Peltier effect thermoelectric cooler PC is mounted in thermal contact with the opposite side of the support plate P, the heated side of which is cooled by the fan F. The proximal end of the lightguide L is directly adjacent or abutting the integrated LED matrix IM, which are of similar cross-section so that the waveguide is not needed to launch the emitted light into the lightguide L.

Figure 8:
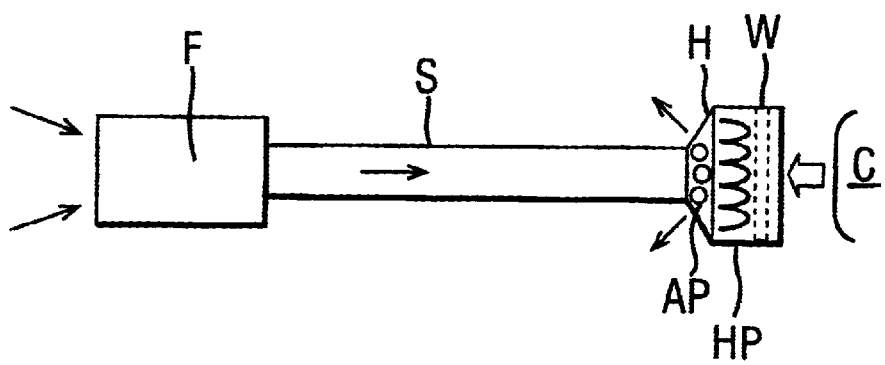
FIG. 8 is a cross-sectional diagram of a fifth embodiment.

A fifth embodiment, as shown in FIG. 8, is designed specifically for treatment of the cervix, such as PDT treatment. The fifth embodiment has the form of a hand piece having a hollow stem S, for example of acrylic or polycarbonate, through which air is blown at low pressure by a fan F mounted at the proximal end. The distal end has a head portion HP comprising a housing within which is mounted a discrete LED array mounted on a support plate/heatsink P/H. Air passes through the hollow stem S onto the heatsink H so as to extract heat therefrom and is then vented through apertures AP on the proximal side of the housing. The distal end of the housing is concave and dimensioned so as to fit closely over the end of the cervix C. A transparent end window W, for example of acrylic or glass, prevents infiltration of the LED's. Power is carried to the LED's through wires (not shown) mounted on the wall of the acrylic stem S. In use, the hand piece is positioned so that the distal end fits over the cervix of the patient and is clamped in position for the duration of the treatment.

The selection of appropriate discrete LED's for PDT using any of the first to fourth embodiments will now be described, grouped according to die material.

A first suitable type of LED is based on aluminium indium gallium phosphide/gallium phosphide (AlInGaP/GaP) of transparent substrate (TS) or absorbing substrate (AS) type. The output wavelengths are in the range 590 to 640 nm with peak emission wavelengths of 590, 596, 605, 615, 626, 630 and 640 nm. Commercially available examples are the 'SunPower'™ or 'Precision Optical Power'™ series from Hewlett Packard Company, designed for use in the automotive industry, for commercial outdoor advertising and traffic management. Suitable LED's are those packaged as: SMT (surface mount technology) e.g. HSMA, HSMB, HSMC, HSML series and preferably HSMB HR00 R1T20 or HSMB HA00R1T2H; Axial e.g. HLMA or HLMT series; T1 e.g. HLMP series, preferably HLMP NG05, HLMP NG07, HLMP J105; T13/4 e.g. HLMP series, preferably HLMP DG08, HLMP DG15, HLMP GG08, HLMP DD16; Superflux™ e.g. HPWA or HPWT series, preferably HPWA (MH/DH/ML/DL) 00 00000, HPWT (RD/MD/DD/BD/RH/MH/DH/BH/RL/ML/DL/BL) 00 00000, most preferably HPWT (DD/DH/DL/MH/ML/MD) 00 00000; SnapLED™ e.g. HPWT, HPWS, HPWL series, preferably HPWT (SH/PH/SL/PL) 00, HPWT (TH/FH/TL/FL) 00 or HPWS (TH/FH/TL/FL) 00. Suitable products from other manufacturers include: of SMT type, Advanced Products Inc. (API) part no. HCL4205AO; of T1 type, American Bright Optoelectronics (ABO) part no. BL BJ3331E or BL BJ2331E; of Superflux type, ABO part no.'s BL F2J23, BL F2J33 and BL F1F33.

A second suitable type of LED is the aluminium indium gallium phosphide/gallium arsenic (AlInGaP/GaAs) type, with emission wavelengths in the range 560 to 644 nm and peak emission wavelengths of 562 nm, 574 nm, 590 nm, 612 nm, 620 nm, 623 nm and 644 nm. Examples commercially available from Toshiba in T1 package are the TLRH, TLRE, TLSH, TLOH or TLYH series, preferably TLRH 262, TLRH 160, TLRE 160, TLSH 1100, TLOH 1100, TLYH 1100 or S4F4 2Q1; or in T13/4 package are the TLRH or TLSH series, preferably TLRH 180P or TLSH 180P. Another example is Kingbright L934SURC-E.

A third suitable type of LED is aluminium gallium arsenic type (AlGaAs), with emission wavelengths in the range 650 to 660 nm. Examples in T1 package include the Toshiba TLRA series, preferably TLRA 290P or TLRA 293P, and Kingbright L934 SRCG, L934 SRCH, and L934 SRCJ and in T13/4 package include Kingbright L53 SRCE.

A fourth suitable type of LED is gallium phosphide (GaP) type, with emission wavelengths in the range 550 to 570 nm.

A fifth suitable type of LED is indium gallium nitride (InGaN). In the type with an emission wavelength of 525 nm, commercially available examples include: in SMT package, API's HCL 1513AG; and in T1 package, Farnell's #942 467, Radio Spare's #228 1879 and #249 8752, API's HB3h 443AG and Plus Opto's NSPG500S. In the type with emission wavelengths of 470 and 505 nm and T1 package type, examples are Farnell's #142 773, Radio Spare's #235 9900 and American Bright Optoelectronics Inc.'s BL BH3PW1.

A sixth suitable type of LED is gallium nitride/silicon (GaN/Si), with an emission wavelength of 430 nm. One commercial example is Siemens LB3336 (also known as RS #284 1386).

Figure 9:
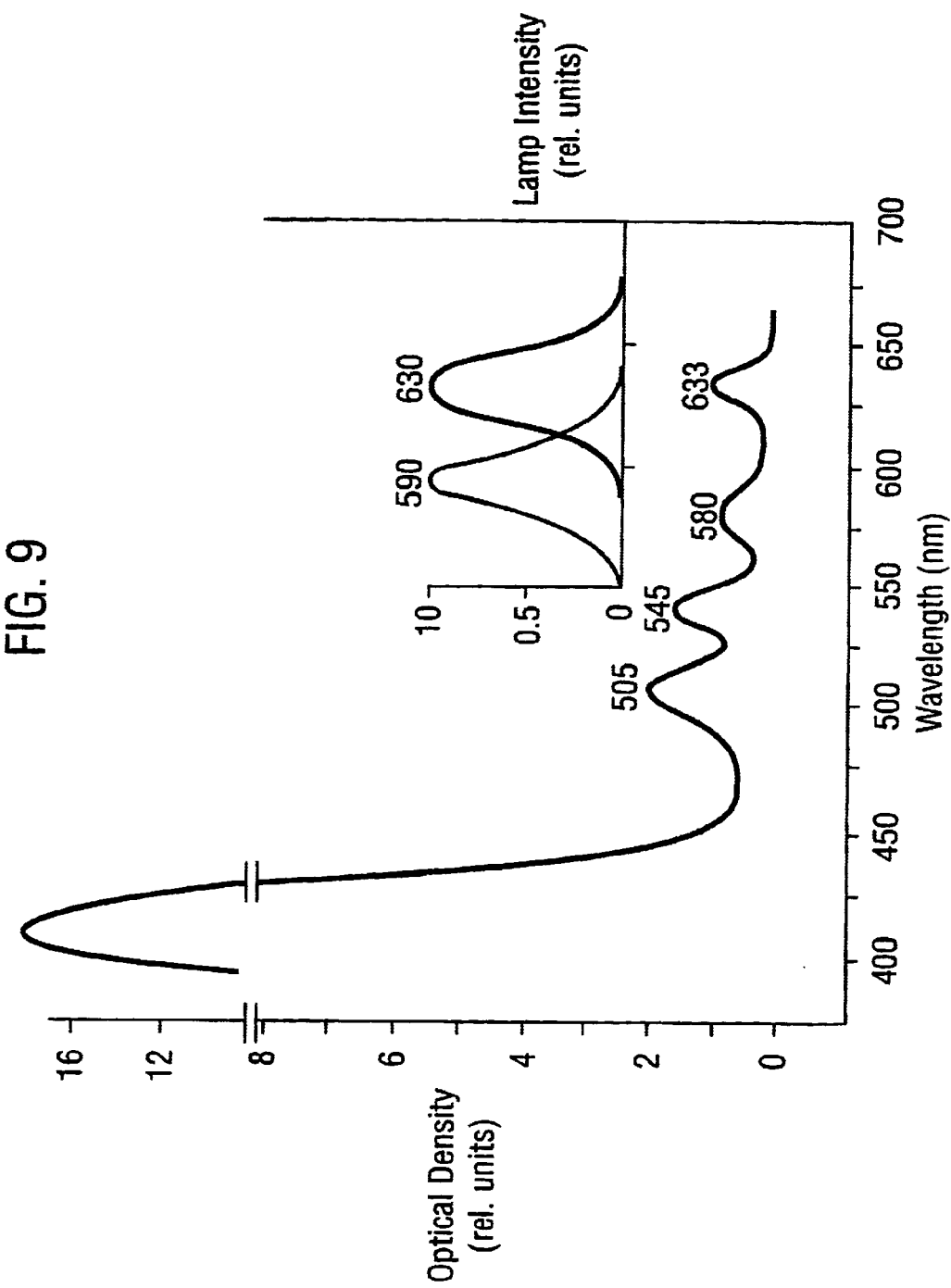
FIG. 9 is a graph showing the absorption spectrum of PpIX and the emission spectra of two examples of LED's suitable for use with the embodiments.

Each of the above LED types is selected to have an emission spectrum substantially coincident with the absorption spectrum of one or more of the following common photosensitizers given below in Table 1, and therefore embodiments having such LED's are suitable for PDT. For example, FIG. 9 shows the absorption spectrum of PpIX, including peaks at 505 nm, 545 nm, 580 nm and 633 nm. Inset are the emission spectra, in units of peak intensity and on the same wavelength axis, of LED part no. HPWA DL00 with a peak at 590 nm and LED part no. HPWT DH00 with a peak at 630 nm, the peaks having sufficient breadth to give a substantial overlap with the 580 nm and 633 nm peaks respectively in the absorption spectrum of PpIX.

TABLE 1

| Photosensitizer | Red absorption Band (nm) | Red Peak (nm) | Blue/Green Peak (nm) |
|---|---|---|---|
| Naphthalocyanines | 780–810 | | |
| Chalcogenopyrilium dyes | 780–820 | | |
| Phthalocyanines (e.g. ZnII Pc) | 670–720 | 690 | |
| Tin etiopurpurin (SnET$_2$) | 660–710 | 660–665 | 447 |
| Chlorins (e.g. N-Aspartyl chlorin e6 or NPe6) | 660–700 | 664 | |
| Benzoporphyrin derivative (BPD) | | 685/690 | 456 |
| Lutetium texaphrin (Lu-Tex) | | 735 | |
| Al(S$_1$/S$_2$/S$_3$/S$_4$) Pc | 660–710 | 670/685 | 410, 480 |
| Photofrin | | 625/630 | 405 |
| Protoporphyrin IX (PpIX) - from 5/δAminolaevulinic Acid (5ALA) | | 635 | 410, 505, 540, 580 |
| Tetra m-hydroxyphenyl Chlorin (mTHPC) | | 650 | 440, 525 |

The discrete LED array may comprise more than one different type of LED, each with different emission spectra, selected to match different absorption bands of the selected photosensitizer. Each type of LED may be switched independently. The penetration depth (i.e. the depth at which the intensity has been attenuated to $e^{-1}$) may also be varied by switching on only one type of LED in the array so as to select a suitable emission band, since the penetration depth is a function of the wavelength.

The LED array may be composed of individually switchable spatially distinct segments of LED's. Selected segments may be switched on so as to treat a selected area of the patient within the overall area of the matrix array.

The lamp may include an electro-optical detector arranged to monitor the light dose delivered and to switch off the light emission when a target dose is reached. Alternatively, or additionally, the detector is arranged to monitor the instantaneous light intensity and to vary the electrical power supplied to the tubes so as to maintain the intensity within predetermined limits, and/or to switch off the light emission if a maximum limit is exceeded.

Various different arrangements of LED array suitable for treatment of different areas of a patient will now be described. The LED's are discrete LED's as described above. Except where stated otherwise, the LED's may be fan-cooled using integrated fans.

Figure 10A:
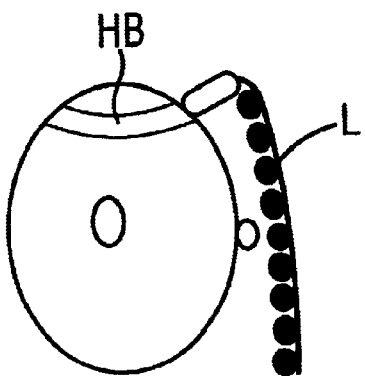
FIGS. 10a and 10b are side and front views respectively of an LED array in a sixth embodiment for treatment of the face.
Figure 10B:
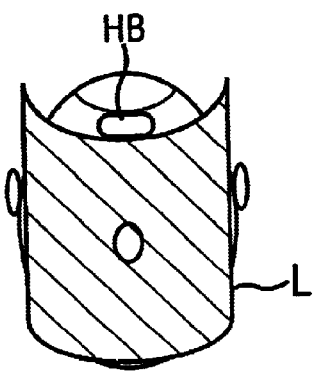

FIGS. 10a and 10b show an array of LED's L in a sixth embodiment, arranged on a support P shaped as a curved visor for treatment of the face of a patient. The array is supported in front of the patient's face by a head band HB or other head wear worn by the patient.

Figure 11A:
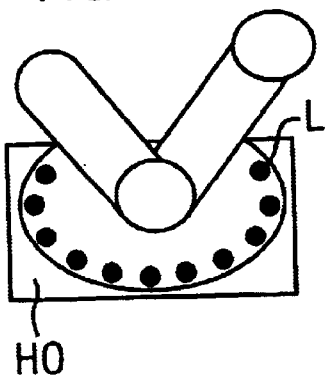
FIGS. 11a, 11b and 11c are a cross-section in the plane of the patient's arm, a top view and a vertical cross-section transverse to the patient's arm of an LED array in a seventh embodiment for treatment of the elbows of a patient.
Figure 11B:
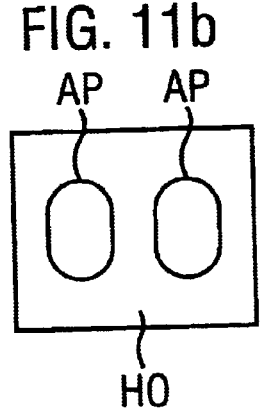
Figure 11C:
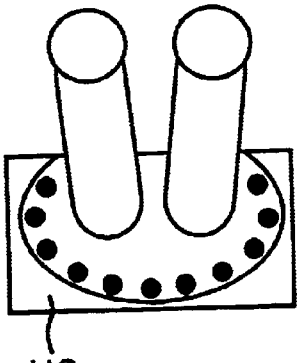

FIGS. 11a to 11c show an array of LED's L in a seventh embodiment arranged within a cuboid housing HO which has two similar apertures AP on one face, to allow the elbows to be inserted into the housing HO. The edges of the apertures AP are cushioned to allow the arms to be rested comfortably. Within the housing HO is arranged a surface SU which is curved both in the plane of the arms and perpendicular to that plane, as shown in FIG. 11c. The LED's L are mounted on this surface SU so that light emitted therefrom is concentrated onto the elbows of the patient.

Figure 12:
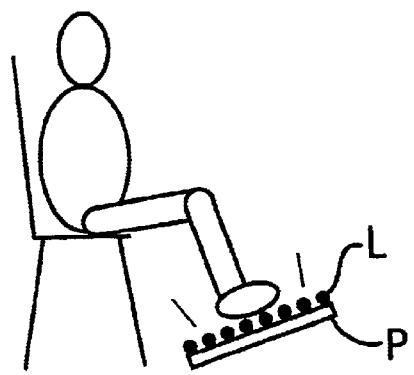
FIG. 12 is a side view of an LED array in an eighth embodiment used for treatment of the foot or feet.

FIG. 12 shows an LED array L in an eighth embodiment mounted on a support plate P, and covered by a transparent or translucent cover on which the foot or feet of the patient rest during treatment.

Figure 13:
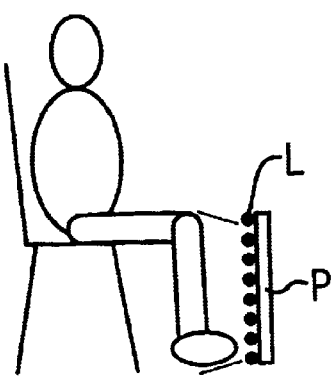
FIG. 13 is a side view of an LED array in a ninth embodiment used for treatment of the lower leg.

FIG. 13 shows an LED array L in a ninth embodiment mounted on a support plate P and arranged for treatment of the lower leg of a patient.

Figure 14:
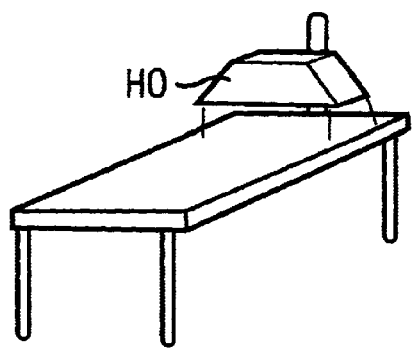
FIGS. 14 and 15 show arrangements of an LED array in tenth and eleventh embodiments for treatment of respectively the face and a section of a patient lying on a bed.
Figure 15:
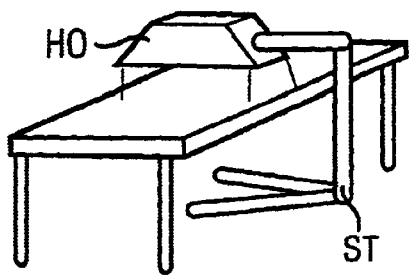

FIGS. 14 and 15 show an LED array L, mounted in a housing HO in the form of a trapezoid prism, the upper inner surface carrying the LED array and the lower surface being open to allow light to fall onto the patient. The side faces may be reflective, or carry additional LED arrays. In the tenth embodiment shown in FIG. 14, the housing HO is mounted at one end of a bed so that its height above the bed is adjustable, for facial treatment of a patient lying on the bed. In the eleventh embodiment shown in FIG. 15, the housing HO is mounted on a stand ST and is adjustable in height, for treatment of a selected part of a patient lying on the bed.

Figure 16A:
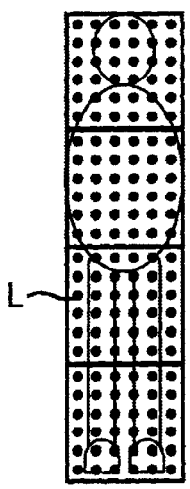
FIGS. 16a and 16b show respectively front and side views of a set of similar LED arrays in an twelfth embodiment for treatment of one side of a patient.
Figure 16B:
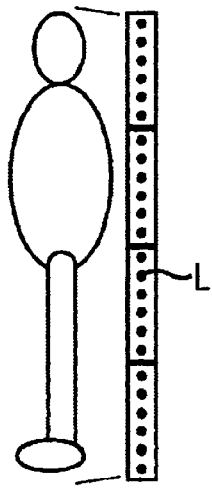

FIGS. 16a and 16b show a series of four coplanar LED arrays L in a twelfth embodiment arranged to treat one side of a patient. Each of the arrays is independently switchable so that selected sections of the patient can be treated.

Figure 17A:
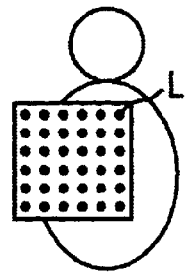
FIGS. 17a and 17b show respectively front and side views of an LED array in a thirteenth embodiment for treatment of a section of one side of a patient.
Figure 17B:
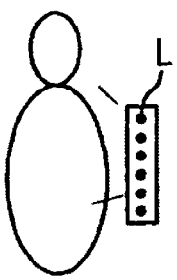

FIGS. 17a and 17b show a single LED array L in a thirteenth embodiment positioned to treat a section of the patient.

Figure 18A:
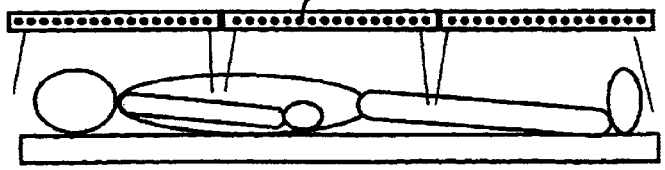
FIGS. 18a and 18b are respectively side and end views of a set of similar LED arrays in a fourteenth embodiment, for treatment of one side of a patient lying down.
Figure 18B:
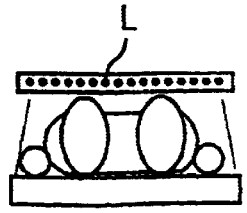

FIGS. 18a and 18b show a series of three coplanar LED arrays L in a fourteenth embodiment arranged to treat one side of a patient lying down. Each of the arrays is independently switchable so that selected sections of the patient can be treated.

Figure 19A:
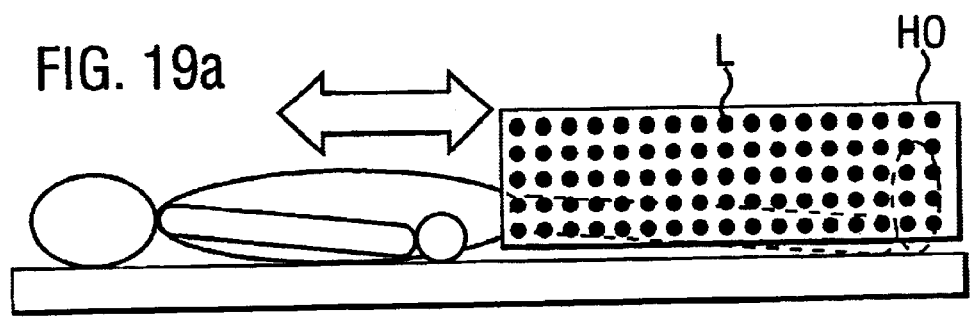
FIGS. 19a and 19b are respectively side and end views of an LED array in a fifteenth embodiment for treatment of a section of a patient lying down.
Figure 19B:
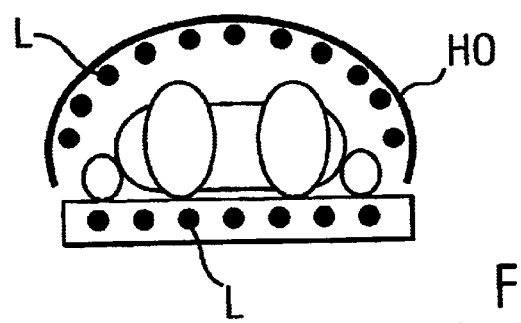

FIGS. 19a and 19b show an array of LED's L in a fifteenth embodiment mounted on the inner surface of a curved housing HO for treatment of a patient lying on a further, planar array of LED's, for treatment of a section of the patient from all sides. The housing HO is slidable along the length of the patient so as to treat a selected area of the patient. Sections of the planar array of LED's are switchable so as to illuminate only the selected section.

Figure 20A:
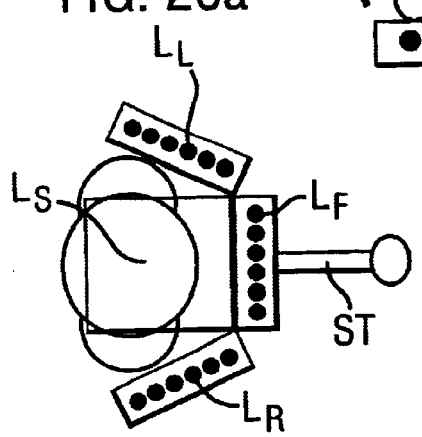
FIGS. 20a and 20b are top and side views respectively of an arrangement of LED arrays in a sixteenth embodiment for treatment of the face and/or scalp.
Figure 20B:
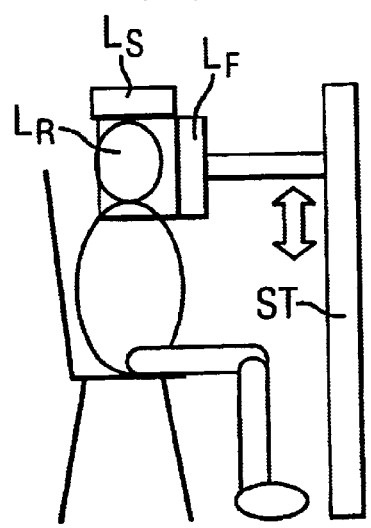

FIGS. 20a and 20b show a sixteenth embodiment comprising a front-facial LED array $L_F$ for directing light onto the face of the patient from the front, a scalp LED array $L_S$ and left and right side-facial LED arrays $L_L$, $L_R$ moveably connected, for example by hinges, to the front-facial array $L_F$, for directing light onto the scalp, left side of the face and right side of the face respectively. The front-facial array $L_F$ is slideably attached to a stand ST for vertical adjustment to the head height of the patient, preferably when sitting.

Figure 21:
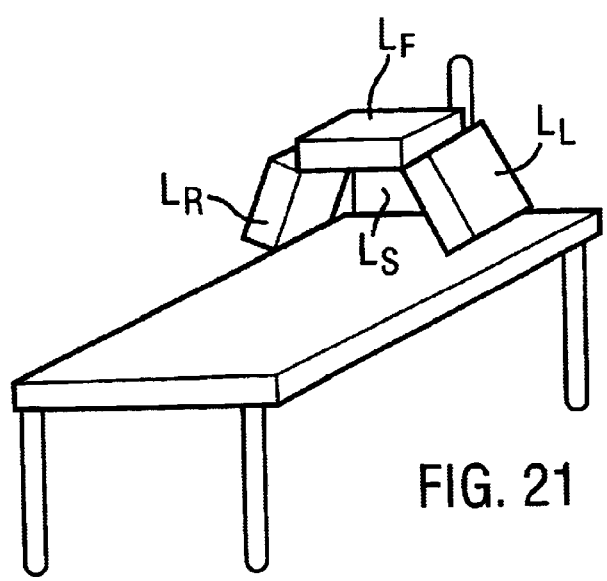
FIG. 21 shows a similar arrangement to that of FIGS. 20*a* and 20*b*, in a seventeenth embodiment for treatment of the face and/or scalp of a patient lying down.

FIG. 21 shows a seventeenth embodiment, similar to that of FIGS. 20a and 20b, except that it is arranged for facial and/or scalp treatment of a patient when lying down. The stand ST is mounted on a bed, instead of being free-standing, and the arrays are rotated by 90° so as to correspond to the position of the patient's head when lying down.

FIGS. 22a, 22b and 22c show an eighteenth embodiment in which an LED array L is mounted on the inner surface of a sleeve SL so as to direct light onto the hand, forearm and/or elbow within the sleeve.

FIGS. 23a and 23b show respectively a square and a rectangular LED array L in a nineteenth embodiment mounted on a flexible backing member FB which can be applied to an area of the patient to be treated, such as part of the forearm as shown in FIG. 23c, with the LED's facing inwardly. The LED array thereby follows the contours of the area to be treated. The flexible backing member FB may be cooled by a fan which is either discrete or connected thereto by a flexible membrane which is fixed around the flexible backing member FB and directs air from a fan onto the backing member, through which the air is vented.

FIG. 24 shows an LED array in a twentieth embodiment arranged on the surface of a cylindrical intraluminal probe, while FIG. 25 shows an LED array in a twenty-first embodiment arranged on the surface of a spherical head of an intraluminal probes. The probes are dimensioned for vulval, cervical, endometrial, bladder, gastrointestinal, oral, nasal, aural and/or bronchial treatment.

In tests performed by the inventor, the efficacy of PDT using red (approximately 630 nm) emission from LED's was established in in-vivo comparative studies using a sub-cutaneous mammary tumour regrowth delay assay. Using radiobiological end-points, it was shown that the solid-state prototype efficacies were comparable to that of expensive conventional lasers for PDT (i.e. no significant difference, p=0.21). These results were confirmed in further clinical studies in the treatment of Bowen's disease and basal cell carcinomas where comparative complete response rates were achieved as compared to laser PDT.

FIG. 26 shows a more specific example of the nineteenth embodiment, consisting of rows of blue LED's $L_B$ interspersed with rows of red LED's $L_R$ so as to form a discrete LED array composed of different types of LED as described above. The blue LED's $L_B$ are switchable on and off together, independently of the red LED's $L_R$ which are also switchable on and off together. In this way, red or blue illumination may be chosen according to the type of treatment and penetration depth required.

The blue LED's have an emission spectrum substantially (for example fill width half maximum bandwidth) in the range 370 to 450 nm, and preferably 400 to 430 nm. This range is particularly suitable for the treatment of pre-cancerous conditions, in particular actinic keratoses.

The red LED's have an emission spectrum substantially (for example full width half maximum bandwidth) in the range 620 to 700 nm. This range is particularly suitable for the treatment of non-melanoma, such as basal cell or squamous cell carcinoma, or mycosis fungoides.

What is claimed is:

1. A light source for therapy or diagnosis of a patient, comprising a housing in the form of a trapezoid prism open at the base and having an upper inner surface carrying an array of light-emitting diodes.

2. A light source as claimed in claim 1, wherein at least one inner side face of the trapezoid prism is reflective.

3. A light source as claimed in claim 1, wherein at least one inner side face of the trapezoid prism carries a further array of light-emitting diodes.

4. A light source for therapy or diagnosis of a patient, comprising an intraluminal probe carrying on a substantially spherical surface thereof an array of discrete light-emitting diodes.

5. A therapeutic light source, comprising an array of light-emitting diodes arranged so that light from the light-emitting diodes is incident directly on a treatment field with an intensity of at least approximately 10 mW/cm$^2$ and a spatial intensity fluctuation of approximately 10% or less, and means for cooling the diodes by forced air convection.

6. A light source as claimed in claim 5, wherein the light-emitting diodes are thermally coupled to one or more heatsinks.

7. A therapeutic light source, comprising an array of light-emitting diodes arranged to give an output intensity of at least 10 mW/cm$^2$ in a treatment field, means for cooling the diodes by forced air convection, and a passage for carrying the air from a proximal end thereof to a distal end thereof, wherein the diodes are mounted at the distal end, the distal end is dimensioned so as to be locatable proximate a cervix such that light emitted by the light-emitting diode array is incident on the cervix, and the distal end is concave so as to fit over the cervix.

8. A light source as claimed in claim 7, including a fan mounted at the proximal end of the passage.

9. A method of cosmetic treatment of a patient, comprising illuminating the treatment area with light from a light source as claimed in any one claims 1, 5, and 7.

10. A method as claimed in claim 9, including applying or administering a photosensitizing drug to the treatment area prior to the illuminating step.

11. A method as claimed in claim 10, for portwine stain removal, or hair restoration or removal.

12. A method as claimed in claim 9, for skin rejuvenation, wrinkle removal or biostimulation.

13. A method of medical treatment of a patient, comprising illuminating the treatment area with light from a light source as claimed in any one of claims 1, 4, 5, and 7.

14. A method as claimed in claim 13, including applying or administering a photosensitizing drug to the treatment area prior to the illuminating step.

15. A method as claimed in claim 14, for the treatment of one or more of actinic/solar keratoses, Bowen's disease, superficial basal cell carcinoma, squamous cell carcinoma, intraepithelial carcinoma, mycosis fungoides, T-cell lymphoma, acne and seborrhoea, eczema, psoriasis, nevus sebaceous, gastrointestinal conditions (e.g. Barratt's oesophagus and colorectal carcinomas), gynaecological disorders (e.g. VIN, CIN and excessive uterine bleeding), oral cancers (e.g. pre-malignant or dyplastic lesions and squamous cell carcinomas), viral infections such as herpes simplex, molluscum contagiosum, and warts (recalcitrant, verruca vulgaris or verruca plantaris), alopecia areata, or hirsutism.

* * * * *